United States Patent [19]

Sato et al.

[11] Patent Number: 5,095,144
[45] Date of Patent: Mar. 10, 1992

[54] PROCESS FOR DIMERIZING AROMATIC HALOGEN COMPOUND

[75] Inventors: Keiichi Sato, Tokyo; Takahiko Takewaki, Kanagawa; Yoshio Katsuro, Fukuoka, all of Japan

[73] Assignee: Mitsubishi Kasei Corporation, Tokyo, Japan

[21] Appl. No.: 553,283

[22] Filed: Jul. 17, 1990

[30] Foreign Application Priority Data

Jul. 18, 1989 [JP] Japan ................................ 1-185071

[51] Int. Cl.$^5$ ................ C07C 63/33; C07C 51/00; C07D 307/77
[52] U.S. Cl. .................... 562/481; 549/241; 562/480; 562/483; 562/487; 562/488; 568/492
[58] Field of Search ............. 549/242, 241, 246; 562/481, 488, 480, 483, 487, 492

[56] References Cited

U.S. PATENT DOCUMENTS

| | | | |
|---|---|---|---|
| 4,727,185 | 2/1988 | Shoji et al. | 562/481 |
| 4,851,583 | 7/1988 | Bockowski et al. | 568/468 |
| 4,900,843 | 2/1990 | Kitai et al. | 549/252 |

FOREIGN PATENT DOCUMENTS 220835 5/1987 European Pat. Off. .
318634 7/1989 European Pat. Off. .

OTHER PUBLICATIONS

Patent Abstract of JP, vol. 1, No. 46, p. 156, JP-5520705.
Patent Abstract of JP, vol. 10, No. 328, JP-61137838.
Patent Abstract of JP, vol. 11, No. 202, JP-6226238.
Peter Bamfield et al., Synthesis Communications, p. 538 (1978).

*Primary Examiner*—Cecilia Shen
*Attorney, Agent, or Firm*—Sughrue, Mion, Zinn, Macpeak & Seas

[57] ABSTRACT

A process for dimerizing an aromatic halogen compound is disclosed, which comprises the step of: subjecting an aromatic halogen compound having at least one halogen atom bonded to an aromatic nucleus carbon to a dehalogenation-dimerization reaction in the presence of a catalyst, water, a reducing agent, and a halogen acceptor, the catalyst comprising a carrier supported thereon palladium and iron.

33 Claims, No Drawings

PROCESS FOR DIMERIZING AROMATIC HALOGEN COMPOUND

FIELD OF THE INVENTION

The present invention relates to a process for producing a dimer of an aromatic halogen compound in a high yield through dehalogenation-dimerization reaction of the aromatic halogen compound.

BACKGROUND OF THE INVENTION

Dimers of aromatic compounds are useful as raw materials in various industrial applications. For example, alkali metal salts of biphenyl-3,4,3',4'-tetracarboxylic acid are extremely useful as a raw material for heat-resistant polyimide resins.

Conventionally known processes for the production of biphenyl compounds through dehalogenation-dimerization reaction of aromatic halogen compounds include, for example, a method in which an aromatic halogen compound is subjected to dehalogenation-dimerization reaction in the presence of a palladium catalyst, water, and methanol (JP-B-59-14015 (the term "JP-B" as used herein means an "examined Japanese patent publication")), and modifications of the above method such as a method in which a polyhydric alcohol or formaldehyde is used in place of methanol (JP-A-62-26238 (the term "JP-A" as used herein means an "unexamined published Japanese patent application")), a method in which formic acid or a formic acid salt is used in place of methanol (*Synthesis Communications*, p. 538 (1978), JP-A-61-137838 and JP-A-61-167642), and a method in which carbon monoxide is used in place of methanol (JP-A-61-293932).

Further, the present inventors previously found that extremely high catalytic activity can be imparted to palladium catalysts for use in dehalogenation-dimerization reactions by treating the catalysts with a hydrohalogenic acid (U.S. Pat. No. 4,900,843).

These methods, however, are defective in that the conversion of the aromatic halogen compound is still insufficient or that even if conversion is satisfactory in the beginning stage of the reactions, the lives of the catalysts are too short. Hence, there has been a desire for development of a catalyst which enables intended biphenyl compounds to be industrially produced in high yields over a prolonged period of time.

SUMMARY OF THE INVENTION

An object of the present invention is to provide a process for producing a biaryl compound in a high yield through the dehalogenation-dimerization reaction of an aromatic halogen compound.

Another object of the present invention is to provide a process for producing a biaryl compound which is carried out in the presence of a catalyst comprising a carrier supported thereon palladium and iron (palladium-iron-supporting catalyst) which is obtained by allowing a palladium compound and an iron compound to be supported on a carrier, and which is suited for dehalogenation-dimerization reactions of aromatic halogen compounds.

Still another object of the present invention is to provide a process for producing, in a high yield, a biphenyl-3,4,3',4'-tetracarboxylic acid compound from 4-chloro-o-phthalic acid or a derivative thereof.

Other objects and effects of the present invention will be apparent from the following description.

The present invention relates to a process for dimerizing an aromatic halogen compound which comprises the step of: subjecting an aromatic halogen compound having at least one halogen atom bonded to an aromatic nucleus carbon to a dehalogenation-dimerization reaction in the presence of a catalyst, water, a reducing agent, and a halogen acceptor, the catalyst comprising a carrier supported thereon palladium and iron.

DETAILED DESCRIPTION OF THE INVENTION

In the process of the present invention, an aromatic halogen compound having at least one halogen atom bonded to an aromatic nucleus carbon is used as a starting material. The at least one halogen atom bonded to an aromatic nucleus carbon may be iodine, bromine, or chlorine, but preferred are bromine and chlorine, with chlorine being particularly preferred because it contributes to low cost. In the case where the aromatic compound has two or more halogen atoms as substituents on the aromatic nucleus or nuclei, these halogen atoms may be the same or different. The number of such halogen atoms can be 6 or less, and an aromatic halogen compound having relatively many halogen atoms may undergo other dehalogenation along with dehalogenation-dimerization The preferred number of halogen atoms is 3 or less.

The aromatic compound may contain a substituent group on the aromatic nucleus other than the above-described at least one halogen atom, particularly one or two carboxyl groups. However, if a carbon atom adjacent to the carbon atom to which a halogen atom is bonded has other substituent group, or if two or more halogen atoms are bonded to carbon atoms adjacent to each other, the yield of the intended biaryl compound may be low.

Specific examples of the above-described aromatic halogen compound used in this invention include chlorobenzene, p-chlorobromobenzene, p-chlorodiphenyl, p-chlorophenol, p-chloroanisole, p-chlorobenzamide, p-chloroaniline, p-chloronitrobenzene, p-chlorobenzophenone, p-chloroacetophenone, sodium p-chlorobenzenesulfonate, p-chlorobenzoic acid and its alkali metal (e.g., lithium, sodium, potassium, etc.) salts, p-chlorobenzonitrile, m-bromobenzoic acid and its alkali metal (e.g., lithium, sodium, potassium, etc.) salts, β-chloronaphthalene, 4-chloro-o-xylene, 4 chloro-o-phthalic acid, 4,5-dichloro-o-phthalic acid and their alkali metal (e.g., lithium, sodium, potassium, etc.) salts, 4-chloro-o-phthalic anhydride, 4,5-dichloro-o-phthalic anhydride, and the like. These may be used either alone or as a mixture thereof.

Of the above compounds, 4-chloro-o-phthalic acid, its alkali metal salts, and its anhydride are particularly advantageous in that use of one of these compounds or use of a mixture mainly containing one of these compounds yields a biphenyl-3,4,3'4'-tetracarboxylic acid alkali metal salt, which is a raw material for a heat-resistant polyimide.

The water may be used in the form of a solution of the above-described aromatic halogen compound in the case where the aromatic halogen compound is water-soluble. Alternatively, the water may be introduced directly into the reaction system. The amount of the water used may usually be 0.1% by volume or more, preferably 1% by volume or more, based on the total amount of the reaction medium containing the aromatic halogen compound, the palladium-iron-supporting catalyst, the reducing agent, and the halogen acceptor. In the case where the aromatic halogen compound is water-soluble, the water is preferably used in a solvent amount.

On the other hand, in the case where the aromatic halogen compound is water-insoluble, it is preferable to use the water in an amount selected from the range of from 1 to 60% by volume because too large a water amount may result in a decrease in the yield of the biaryl compound. If the amount of the water used is smaller than the lower limit as specified above or if no water is added, the yield and selectivity of the biaryl compound tend to be lowered disadvantageously.

Examples of the reducing agent used in the present invention generally include methanol, polyhydric alcohols such as, for example, ethylene glycol, glycerin and erythritol, formaldehyde and its derivatives, formic acid and its salts, and the like. Preferred of these reducing agents are polyhydric alcohols having from 2 to 4 carbon atoms such as ethylene glycol, glycerin, etc.

The amount of the reducing agent used may generally be from 0.01 to 50 mol, preferably from 0.1 to 10 mol, per mol of the aromatic halogen compound. Carbon monoxide may also be used as the reducing agent. In this case, the carbon monoxide pressure is not particularly limited, but it may generally be from 0.001 to 150 $kg/cm^2$ in terms of the partial pressure of carbon monoxide. If the amounts of the reducing agents are outside of the above ranges, the yield of the intended biaryl compound tends to be lowered. Methods of using these reducing agents are not particularly limited; a predetermined amount, within the above-specified range, of the reducing agent may be added to the reaction system at a time, or may be fed continuously or intermittently during the dehalogenation dimerization reaction.

In the process of the present invention, use of a halogen acceptor is necessary for attaining high yields of biaryl compounds. As the halogen acceptor, any substance that can accept halogen atoms resulting from the dehalogenation-dimerization reaction can be employed. Generally, a basic substance may be used as the halogen acceptor. Examples of the basic substance include ammonia, alkali metal compounds, alkaline earth metal compounds, and the like. Of these, alkali metal compounds and alkaline earth metal compounds are preferred, and specific examples of such preferred alkali metal or alkaline earth metal compounds include hydroxides, salts of inorganic acids such as carbonic acid, nitric acid, phosphoric acid, and boric acid, salts of organic acids such as acetic acid and phthalic acid, alkoxides, and the like.

Particularly preferred examples of the halogen acceptor include hydroxides such as lithium hydroxide, sodium hydroxide, potassium hydroxide, magnesium hydroxide, calcium hydroxide, barium hydroxide, and the like, carbonates such as sodium carbonate, potassium carbonate, sodium hydrogen carbonate, and the like, and lower ($C_1$-$C_4$) alkoxides such as sodium methoxide, sodium ethoxide, potassium tert-butoxide, and the like. Hydroxides are more preferred because carbonates may bring about slightly lower reaction yields than hydroxides.

The amount of the halogen acceptor used is varied depending on the number of halogen atoms contained in the aromatic halogen compound as the starting material and also on the presence of an acidic substituent such as carboxyl group, and thus is not particularly limited. Generally, however, the halogen acceptor is used in an amount of 0.01 to 100 mol, preferably 0.1 to 20 mol, per mol of the aromatic halogen compound. If the amount of the halogen acceptor used is outside of the above range the yield of the biaryl compound is lowered and other unfavorable results are produced.

The palladium-iron-supporting catalyst used in the present invention is one obtained by allowing a palladium compound and an iron compound to be supported on a carrier. Examples of the carrier include active carbon, silica, alumina, silica-alumina, titanium oxide, magnesia, diatomaceous earth, graphite, barium carbonate, calcium carbonate, zeolite, zirconia, and the like, with active carbon being particularly preferred.

Examples of the palladium compound include halogen-containing palladium compounds such as ammonium tetrachloropalladate, palladium salts of inorganic acids such as palladium bromide, palladium chloride, and palladium nitrate, palladium salts of organic acids such as palladium acetate and palladium propionate, organic palladium complex salts such as $PdCl_2(C_6H_5CN)_2$, $PdCl_2(CH_5N)_2$, and palladium acetylacetonate, and the like. Of these, palladium chloride and tetrachloropalladates are particularly preferred. The amount of the palladium supported on the carrier may generally be from 0.1 to 20% by weight, preferably from 0.5 to 10% by weight, in terms of the amount of metallic palladium, based on the amount of the carrier.

Examples of the iron compound include halides of iron such as iron chloride and iron bromide, iron salts of inorganic acids such as iron nitrate, iron salts of organic acids such as iron acetate, organic iron complex salts such as iron acetylacetonate, and the like. Of these, chlorides such as ferrous chloride and ferric chloride are preferred. The amount of the iron supported on the carrier may generally be from 0.05 to 5 gram-atoms, preferably about 0.5 to 3 gram-atoms, in terms of the amount of metallic iron, per gram-atom of the palladium.

Methods of allowing the palladium compound and iron compound to be supported on the carrier are not particularly limited, and ordinarily employed methods may be used.

For example, preferably employed methods include an evaporation-to-dryness method in which a carrier is immersed in a solution containing the above-described metal compounds, and then the solvent is evaporated with stirring, thereby fixing the metal compounds on the carrier; a method in which a carrier is immersed in a solution containing the metal compounds, and the carrier is then filtered off; and other known methods for fixing metal compounds on carriers. In these fixing methods, the palladium compound and iron compound may be fixed simultaneously or one after the other.

A particularly preferred fixing method comprises adding a carrier to an aqueous hydrohalogenic acid solution containing the above-described palladium compound and iron compound to allow the carrier to be impregnated with the compounds and to support the compounds at room temperature, subsequently adding an alkali such as sodium hydroxide to the above-obtained slurry to make the solution alkaline, and then separating the resulting carrier by an ordinarily employed means such as filtration, thereby obtaining a catalyst having palladium and iron supported on the carrier.

This palladium-iron-supporting catalyst may be used as it is in dimerization reactions, or may be used after being dried or treated with a reducing agent such as hydrogen. It is preferable to conduct the drying, for example, in a calcium chloride desiccator or in a nitrogen stream of from 70° to 300° C., because of the easiness of the procedures. It is also preferable, if desired, that the catalyst be activated by a post-treatment such as calcining treatment in an air stream at from 70° to 300° C. or reducing treatment in a hydrogen stream at from 20° to 500° C.

Besides the above-described method in which the carrier is allowed to be impregnated with the palladium compound and iron compound and to support the compounds in an aqueous hydrohalogenic acid solution, there may also be employed a method in which a metallic palladium-supporting catalyst is added to an aqueous hydrohalogenic acid solution containing the iron compound, thereby allowing the catalyst to be impregnated with the iron compound and to support the compound.

Examples of the hydrohalogenic acid include hydrochloric acid, hydrobromic acid, and the like, but hydrochloric acid is especially preferred. The amount of the hydrohalogenic acid used is not particularly limited as long as it is used in such an amount that the slurry containing the palladium compound, iron compound, and carrier can be kept acidic. Examples of the alkali, which is added to the slurry in which the carrier has been allowed to be impregnated with and support the palladium compound and iron compound, include hydroxides of alkali metals or alkaline earth metals, alkali metal salts or alkaline earth metal salts of carbonic acid, and the like. The alkali may be added in an amount that is necessary for making the slurry to be alkaline, preferably to have a pH of 8 or higher, more preferably from 8 to 12.

The catalyst thus prepared not only enables intended biaryl compounds to be obtained in high yields, but suffers only a slight decrease in catalytic activity, as compared with catalysts on which palladium only is supported. Therefore, the palladium-iron-supporting catalyst, when employed in the process of the present invention, ensures stable production of biaryl compounds over a prolonged period of time and is, hence, of considerable industrial usefulness.

The amount of the palladium-iron-supporting catalyst used may generally be from 100 to 0.001 milligram-atom, preferably from 30 to 0.1 milligram-atom, in terms of the amount of palladium atom, per mol of the aromatic halogen compound.

The dehalogenation-dimerization reaction of an aromatic halogen compound may be conducted in either the presence or absence of a solvent. In the case where the reaction is carried out in the presence of a solvent, the solvent should be inert in the reaction.

Such an inert solvent may be selected from ethers such as tetrahydrofuran and dioxane, ketones such as acetone, diethyl ketone, and methyl ethyl ketone, esters such as ethylene glycol diacetate, and the like. The amount of such a solvent is not particularly limited, but is generally in the range of from 0.01 to 100 parts by weight per part by weight of the aromatic halogen compound.

The process of the present invention can be carried out by heating a liquid mixture comprising the above-described aromatic halogen compound, palladium-iron-supporting catalyst, water, reducing agent, and halogen acceptor at a temperature of generally from 20° to 250° C., preferably from 50° to 200° C., in the presence or absence of a solvent. The reaction pressure is generally in the range of from ordinary pressure to 200 kg/cm$^2$, preferably from ordinary pressure to 100 kg/cm$^2$. If necessary, the reaction is effected in the presence of an inert gas. The reaction time is not particularly limited, and is suitably fixed according to the kind of the raw material, the amount of the catalyst, the temperature and pressure for the reaction, etc. Normally, however, the reaction is carried out for about from 10 minutes to 24 hours, and preferably 1 to 10 hours.

The process of the present invention can be practiced batchwise, semi-batchwise, or continuously.

The biaryl compound produced by the dehalogenation dimerization reaction described above is separated from the reaction mixture by conventional methods such as evaporation, distillation, crystallization, separating with acid, etc., according to the physical properties of the biaryl compound.

The present invention will be described in more detail by reference to the following Examples, which should not be construed to be limiting the scope of the invention.

EXAMPLE 1

Preparation of Catalyst

In 15 ml of ethanol were dissolved sodium tetrachloropalladate in an amount of 0.85 milligram-atom in terms of the amount of palladium atom and ferric chloride hexahydrate in an amount of 0.425 milligram-atom in terms of the amount of iron atom. To this solution was added 2.9 g of active carbon. After the resulting mixture was stirred for 24 hours at room temperature, the solvent was removed in an $N_2$ stream. The residue was dried at 150° C. for 1 hour in an $N_2$ stream, and then subjected to reducing treatment in a hydrogen stream at 450° C. for 6 hours. Thus, a palladium-iron-supporting active carbon catalyst was obtained.

Dimerization

Into a 200-ml Erlenmeyer flask made of Pyrex glass were introduced 30 g of a white powder composed mainly of monosodium 4-chlorophthalate, 50 ml of desalted water, and 7 g of 95-wt. % sodium hydroxide. The contents were stirred with a magnetic stirrer to dissolve the solid ingredients. To this solution was then added 0.4 g of active carbon, and the resulting mixture was stirred for 3 hours and then filtered. Desalted water was added to the filtrate to adjust the total volume of the filtrate to 100 ml. A 10-ml portion of the diluted filtrate was used below as a raw material solution containing sodium 4-chlorophthalate. (10 Milliliters of the raw material solution contained 7.18 mmol of sodium 4-chlorophthalate, 2.83 mmol of sodium phthalate, 0.49 mmol of sodium: 4,5-dichlorophthalate, 1.52 mmol of sodium 3-chlorophthalate, and 0.38 mmol of sodium 3,4-dichlorophthalate.)

Subsequently, 10 ml of the above-obtained raw material solution, 0.24 g of the palladium-iron-supporting active carbon prepared above, 0.7 g of 95-wt. % sodium hydroxide, and 0.48 g of glycerin were placed in a micro-autoclave made of SUS316 and having a capacity of 70 ml. After the air in the autoclave was replaced with nitrogen, the pressure in the autoclave was regulated at a nitrogen pressure of 2.0 kg/cm$^2$G. Reaction was then allowed to proceed with heating at 150° C. for 2 hours while the autoclave was being revolved with a magnetic stirrer. After completion of the reaction, the resulting reaction mixture was analyzed by liquid chromatography and, as a result, it was found that the desired sodium salt of biphenyl-3,4,3',4'-tetracarboxylic acid (hereinafter abbreviated as "S-BTC") had been formed in the liquid reaction mixture. The results obtained are shown in Table 1.

COMPARATIVE EXAMPLE 1

The same procedures as in Example 1 were repeated except that ferric chloride hexahydrate was not used in the Preparation of Catalyst.

EXAMPLE 2

In 118 ml of a 5.6 wt. % aqueous solution of hydrochloric acid were dissolved palladium dichloride in an amount of 0.85 milligram-atom in terms of the amount of palladium atom and ferric chloride in an amount of 0.85 milligram-atom in terms of the amount of iron atom. To this solution was added 4.4 g of active carbon. After the resulting slurry was stirred for 24 hours at room temperature, a 30 wt. % aqueous solution of sodium hydroxide wa added to adjust the pH of the slurry to 11. This slurry was further stirred for 24 hours, and then the solid matter was filtered off and washed sufficiently with desalted water (the presence of either palladium or iron in the filtrate was not detected). After the washing, the solid matter filtered off was dried in a calcium chloride desiccator for 1 hour at a reduced pressure, and then subjected to reducing treatment in a hydrogen stream at 300° C. for 3 hours, thereby obtaining a palladium-iron-supporting active carbon catalyst. Using this catalyst, dimerization reaction was carried out in the same manner as in Example 1. The results obtained are shown in Table 1.

EXAMPLE 3

Catalyst preparation and dimerization reaction were conducted in the same manner as in Example 2 except that the amount of ferric chloride used was changed to 0.425 milligram-atom in terms of the amount of iron atom and that the reducing treatment was performed at 450° C. for 6 hours in a hydrogen stream. The results obtained are shown in Table 1.

TABLE 1

| | Fe/Pd atomic ratio | Conversion of 4-chlorophthalate* (mol %) | Yield of S-BTC** (mol %) |
|---|---|---|---|
| Example 1 | 0.5 | 81 | 30 |
| Example 2 | 1 | 100 | 69 |
| Example 3 | 0.5 | 100 | 62 |
| Comparative Example 1 | 0 | 29 | 5 |

Note:
*Conversion (mol %):

$$\frac{\text{(Introduced amount of 4-chlorophthalate (mmol))} - \text{Remaining amount of 4-chlorophthalate (mmol))}}{\text{(Introduced amount of 4-chlorophthalate (mmol))}} \times 100$$

**Yield of S-BTC (mol %):

$$\frac{\text{(Yielded amount of S-BTC (mmol))}}{\text{(Introduced amount of 4-chlorophthalate (mmol) + Introduced amount of 4,5-dichlorophthalate (mmol))}} \times 100$$

It can be understood from the results in Table 1 above that by the method according to the present invention, a biaryl compound can be producing in a high yield.

EXAMPLE 4

Immersion Treatment of Catalyst

Into a 500-ml beaker made of Pyrex glass were introduced 400 ml of desalted water and 0.676 g (4.17 mmol) of ferric chloride. After the ferric chloride was dissolved in the water, 35% hydrochloric acid was added to adjust the pH of the solution to 0.82. Subsequently, 0.90 wt. %-palladium carbon (containing 55.1 wt. % water; manufactured by N. E. Chemcat Co.) was added in an amount of 49.42 g (corresponding to 44.33 mg (4.17 mmol) of Pd), and the resulting mixture was stirred for 30 minutes with a magnetic stirrer. The pH of this mixture was then adjusted to 11 with a 25 wt. % aqueous solution of caustic soda, and the resulting slurry was stirred for 10 minutes. From the slurry, the palladium-iron-supported carbon was separated by filtration with a 5C filter paper (produced by Toyo Roshi K.K., Japan), thereby obtaining an immersion-treated palladium-iron-supporting catalyst.

1st Reaction

Dimerization

Into a stainless-steel autoclave having a capacity of 1.5 liters and equipped with an induction stirrer were introduced the immersion-treated palladium-iron-supporting catalyst obtained above, 691.3 g of an aqueous solution of crude 4-chlorophthalic acid (containing 812.9 mmol of disodium 4-chlorophthalate, 98.8 mmol of disodium 4,5-dichlorophthalate, 15.2 mmol of disodium 3-chlorophthalate, 8.0 mmol of disodium 3,4-dichlorophthalate, 121.3 mmol of disodium phthalate, and 459.8 mmol of caustic soda), 160.4 g of a 47 wt. % aqueous solution of caustic soda (1,884 mmol), 244.4 ml of desalted water, and 19.2 g (208.5 mmol) of glycerin. The resulting mixture was heated with stirring at 108° C. for 5 hours in a nitrogen atmosphere, thereby allowing reactions to proceed.

Reducing Treatment

Stirring of the above-obtained reaction mixture was further continued for 1 hour in a hydrogen atmosphere, while the pressure in the autoclave was kept at 9.5 kg/cm$^2$G and the temperature at 150° C. Thereafter, the reaction mixture was cooled and diluted with desalted water, and then the palladium-iron-supporting catalyst was filtered off.

The liquid reaction mixture taken after completion of the dimerization reaction was analyzed by liquid chromatography to determine the conversion of disodium 4-chlorophthalate and that of disodium 4,5-dichlorophthalate. Also, the liquid reaction mixture from which the catalyst had been removed by filtration after the reducing treatment was analyzed likewise to determine the yield of S-BTC. The results obtained are shown in Table 2.

2nd and 3rd Reactions

Dimerization reaction was carried out in the same manner as in 1st Reaction except that the catalyst recovered in 1st Reaction was used, and then the palladium-iron-supporting catalyst was recovered (2nd Reaction). The same procedures were repeated (3rd Reaction).

4th Reaction

Dimerization reaction was carried out in the same manner as in 1st Reaction except that the catalyst which had been recovered after the repeated three-time use in the above 1st to 3rd Reactions was used. The conversion of disodium 4-chlorophthalate, that of disodium 4,5-dichlorophthalate, and the yield of S-BTC were determined. The results obtained are shown in Table 2.

COMPARATIVE EXAMPLE 2

The same procedures as in Example 4 were repeated except that ferric chloride was not added in the Immersion Treatment of Catalyst. Analytical data for the 1st and 4th Reactions are shown in Table 2.

TABLE 2

| | Reaction | Conversion of disodium 4-chlorophthalate* (mol %) | Conversion of disodium 4,5-dichlorophthalate* (mol %) | Yield of S-BTC** (mol %) |
|---|---|---|---|---|
| Example 4 | 1st | 100 | 100 | 74.2 |
| Example 4 | 4th | 100 | 100 | 72.2 |
| Comparative Example 2 | 1st | 100 | 100 | 73.7 |
| Comparative Example 2 | 4th | 100 | 70.7 | 67.1 |

Note:
*Conversion (mol %):
$$\frac{(\text{Introduced amount (mmol)} - \text{Remaining amount (mmol)})}{(\text{Introduced amount (mmol)})} \times 100$$

**Yield (mol %):
$$\frac{(\text{Yielded amount of S-BTC (mmol)})}{(\text{Introduced amount of 4-chlorophthalate (mmol)} + \text{Introduced amount of 4,5-dichlorophthalate (mmol)})} \times 100$$

It can be understood from the results in Table 2 above that by the method according to the present invention, an biaryl compound can be producing in a high yield even if the catalyst is that after repeated use.

While the invention has been described in detail and with reference to specific embodiments thereof, it will be apparent to one skilled in the art that various changes and modifications can be made therein without departing from the spirit and scope thereof.

What is claimed is:

1. A process for dimerizing an aromatic halogen compound which comprises the step of: subjecting an aromatic halogen compound having at least one halogen atom bonded to an aromatic nucleus carbon, where the aromatic nucleus contains only carbon atoms in any aromatic ring thereof, to a dehalogenation-dimerization in the presence of a catalyst, water, a reducing agent, and a halogen acceptor, said catalyst comprising a carrier having supported thereon palladium and iron.

2. A process as claimed in claim 1, wherein the amount of the palladium supported on the carrier is from 0.1 to 20% by weight, in terms of the amount of metallic palladium, based on the amount of the carrier.

3. A process as claimed in claim 1, wherein the amount of the iron supported on the carrier is from 0.05 to 5 gram-atoms, in terms of the amount of metallic iron, per gram-atom of the palladium.

4. A process as claimed in claim 1, wherein the amount of the palladium supported on the carrier is from 0.5 to 10% by weight, in terms of the amount of metallic palladium, based on the amount of the carrier and the amount of the iron supported on the carrier is from 0.5 to 3 gram-atoms, in terms of the amount of metallic iron, per gram-atom of the palladium.

5. A process as claimed in claim 1, wherein said aromatic halogen compound has three or less bromine or chlorine atoms on the aromatic nucleus or nuclei.

6. A process as claimed in claim 1, wherein said aromatic halogen compound has a chlorine or bromine atom and one or two carboxyl groups.

7. A process as claimed in claim 1, wherein said aromatic halogen compound is at least one member selected from the group consisting of 4-chloro-o-phthalic acid, 4,5-dichloro-o-phthalic acid, alkali metal salts of said acids, and anhydrides of said acids.

8. A process as claimed in claim 1, wherein said reducing agent is selected from the group consisting of methanol, formaldehyde, formic acid, salts of formic acid, and polyhydric alcohols having 2 to 4 carbon atoms.

9. A process as claimed in claim 1, wherein said reducing agent is ethylene glycol or glycerin.

10. A process as claimed in claim 1, wherein said reducing agent is glycerin.

11. A process as claimed in claim 1, wherein said halogen acceptor is selected from the group consisting of ammonia, hydroxides of alkali metals, hydroxides of alkaline earth metals, ammonia, alkali metal or alkaline earth metal salts of inorganic acids, ammonia, alkali metal or alkaline earth metal salts of organic acids, and alkoxides having 1 to 4 carbon atoms.

12. A process as claimed in claim 1, wherein said halogen acceptor is selected from the group consisting of hydroxides of alkali metals, hydroxides of alkaline earth metals, ammonia, alkali metal or alkaline earth metal salts of carbonic acid, and alkoxides having 1 to 4 carbon atoms.

13. A process as claimed in claim 1, wherein said halogen acceptor is an alkali metal hydroxide.

14. A process as claimed in claim 1, wherein said catalyst is prepared by
 (i) (a) adding a carrier to an aqueous hydrohalogenic acid solution containing a palladium compound and an iron compound or (b) adding a metallic palladium-supporting catalyst to a hydrohalogenic acid solution containing an iron compound, to form a slurry,
 (ii) adding an alkali to the above-obtained slurry to make the slurry alkaline,
 (iii) subsequently separating the carrier which has been impregnated with the palladium compound and the iron compound, and
 (iv) then drying the carrier.

15. A process as claimed in claim 14, wherein said palladium compound is selected from the group consisting of halogen-containing palladium compounds, palladium salts of inorganic acids, palladium salts of organic acids, and organic palladium complex salts.

16. A process as claimed in claim 14, wherein said palladium compound is palladium chloride or a tetrachloropalladate.

17. A process as claimed in claim 14, wherein said iron compound is selected from the group consisting of halides of iron, iron salts of inorganic acids, iron salts of organic acids, and organic iron complex salts.

18. A process as claimed in claim 14, wherein said iron compound is a chloride of iron.

19. A process as claimed in claim 14, wherein said catalyst is prepared by
 (i) (a) adding a carrier to an aqueous hydrohalogenic acid solution containing a palladium compound and an iron compound or (b) adding a metallic palladium-supporting catalyst to a hydrohalogenic acid solution containing an iron compound, to form a slurry,
 (ii) adding an alkali to the above-obtained slurry to adjust the pH of the slurry to 8 to 12,
 (iii) subsequently separating the carrier containing the palladium and iron from the slurry,
 (iv) drying the carrier, and (v) then subjecting the carrier obtained above to a reducing treatment.

20. A process as claimed in claim 19, wherein said reducing treatment is performed at a temperature of from 20° to 500° C. in a hydrogen stream.

21. A process as claimed in claim 19, wherein said palladium compound is selected from the group consisting of halogen-containing palladium compounds, palladium salts of inorganic acids, palladium salts of organic acids, and organic palladium complex salts.

22. A process as claimed in claim 19, wherein said palladium compound is palladium chloride or a tetrachloropalladate.

23. A process as claimed in claim 19, wherein said iron compound is selected from the group consisting of halides of iron, iron salts of inorganic acids, iron salts of organic acids, and organic iron complex salts.

24. A process as claimed in claim 19, wherein said iron compound is a chloride of iron.

25. A process as claimed in claim 1, wherein the dimerization reaction is carried out at from 20° to 250° C. under a pressure of from ordinary pressure to, 200 kg/cm$^2$.

26. A process as claimed in claim 1, wherein said catalyst is used in an amount of from 100 to 0.001 milligram-atom, in terms of the amount of palladium atom, per mole of the aromatic halogen compound.

27. A process as claimed in claim 1, wherein said catalyst is prepared by
(i) (a) adding a carrier to an aqueous hydrohalogenic acid solution containing a palladium compound and an iron compound or (b) adding a metallic palladium-supporting catalyst to a hydrohalogenic acid solution containing an iron compound, to form a slurry,
(ii) subsequently separating the carrier which has been impregnated with the palladium compound and the iron compound, and
(iii) then drying the carrier.

28. A process as claimed in claim 14, wherein said carrier is active carbon.

29. A process as claimed in claim 27, wherein said carrier is active carbon.

30. A process as claimed in claim 15, wherein said palladium salts of inorganic acids are selected from the group consisting of palladium bromide, palladium chloride, and palladium nitrate, said palladium salts of organic acids are selected from the group consisting of palladium acetate and palladium propionate, and said organic palladium complex salts are selected from the group consisting of $PdCl_2(C_6H_5CN)_2$, $PdCl_2(C_5H_5N)_2$ and palladium acetylacetonate.

31. A process as claimed in claim 17, wherein said iron salts of inorganic acids is iron nitrate, said iron salts of organic acids is iron acetate and said iron complex salts is iron acetylacetonate.

32. A process as claimed in claim 21, wherein said palladium salts of inorganic acids are selected from the group consisting of palladium bromide, palladium chloride, and palladium nitrate, said palladium salts of organic acids are selected from the group consisting of palladium acetate and palladium propionate, and said organic palladium complex salts are selected from the group consisting of $PdCl_2(C_6H_5CN)_1$, $PdCl_2(C_5H_5N)_2$ and palladium acetylacetonate.

33. A process as claimed in claim 23, wherein said iron salts of inorganic acids is iron nitrate, said iron salts of organic acids is iron acetate and said iron complex salts is iron acetylacetonate.

* * * * *